US012364572B2

(12) United States Patent
Suniga et al.

(10) Patent No.: US 12,364,572 B2
(45) Date of Patent: Jul. 22, 2025

(54) EQUIPMENT ADAPTOR ASSEMBLY AND EQUIPMENT STAND

(71) Applicant: Potrero Medical, Inc., Hayward, CA (US)

(72) Inventors: Hannah Jackson Suniga, San Diego, CA (US); Rich Keenan, Granite Bay, CA (US); Mark Ziegler, San Bruno, CA (US)

(73) Assignee: Potrero Medical, Inc., Hayward, CA (US)

( * ) Notice: Subject to any disclaimer, the term of this patent is extended or adjusted under 35 U.S.C. 154(b) by 0 days.

(21) Appl. No.: 18/350,501

(22) Filed: Jul. 11, 2023

(65) Prior Publication Data

US 2023/0346510 A1    Nov. 2, 2023

Related U.S. Application Data

(63) Continuation of application No. PCT/US2022/013701, filed on Jan. 25, 2022.

(60) Provisional application No. 63/141,692, filed on Jan. 26, 2021.

(51) Int. Cl.
*A61B 90/57* (2016.01)
*A61B 5/20* (2006.01)

(52) U.S. Cl.
CPC .............. *A61B 90/57* (2016.02); *A61B 5/208* (2013.01); *A61B 2090/571* (2016.02)

(58) Field of Classification Search
CPC ... A61B 90/57; A61B 5/208; A61B 2090/571; A61J 1/10; A61J 2200/76; A61J 1/16; A61M 5/1415; A61M 5/1417; A61G 7/0503; A61G 13/102
See application file for complete search history.

(56) References Cited

U.S. PATENT DOCUMENTS

| | | | | |
|---|---|---|---|---|
| 5,891,051 | A * | 4/1999 | Han | A61B 5/208 600/580 |
| 6,182,662 | B1 | 2/2001 | McGhee | |
| 6,481,679 | B1 * | 11/2002 | Bennett | F16M 13/022 248/223.41 |

(Continued)

FOREIGN PATENT DOCUMENTS

| WO | WO 2019/246126 | 12/2019 |
|---|---|---|
| WO | WO 2022/164801 | 8/2022 |

*Primary Examiner* — Ko H Chan
(74) *Attorney, Agent, or Firm* — Levine Bagade Han LLP

(57) ABSTRACT

Equipment adaptor assembly and equipment stands are described where the adaptor may generally comprise an adaptor body having a width and a depth, and a connector extending from the adaptor body configured for securement to the equipment. A first recess may be defined by a brace positioned at a first location along the adaptor body, and a second recess may be defined at a second location at a distance from the first recess. The adaptor may be further configured to be interchangeably securable to a support structure via the first recess or second recess while maintaining a level orientation of the equipment such that securement via the first recess positions the equipment at a first height relative to horizontal and securement to the support structure via the second recess positions the equipment at a second height relative to horizontal where the first height and second height are different.

22 Claims, 16 Drawing Sheets

(56) References Cited

U.S. PATENT DOCUMENTS

| | | | |
|---|---|---|---|
| 7,546,993 B1* | 6/2009 | Walker | F16M 11/24 |
| | | | 248/229.12 |
| 7,859,853 B2* | 12/2010 | Schmeisser | G06F 1/1626 |
| | | | 361/752 |
| 10,292,883 B2* | 5/2019 | Jepsen | A61G 7/0503 |
| 11,911,160 B2* | 2/2024 | Woodard | A61B 5/0022 |
| 12,097,150 B2* | 9/2024 | Chancy | A61G 7/05 |
| 2007/0267550 A1 | 11/2007 | Blankenship et al. | |
| 2009/0314923 A1 | 12/2009 | Timoszyk et al. | |
| 2010/0276556 A1* | 11/2010 | Locke | F16M 11/046 |
| | | | 248/207 |
| 2011/0121149 A1* | 5/2011 | Herskovic | A61G 7/0503 |
| | | | 248/223.41 |
| 2014/0231605 A1* | 8/2014 | Sharpe | F16B 2/065 |
| | | | 248/228.6 |
| 2017/0215979 A1 | 8/2017 | Childs et al. | |
| 2020/0155394 A1 | 5/2020 | Weaver | |
| 2023/0054937 A1* | 2/2023 | Chancy | A61G 7/05 |

* cited by examiner

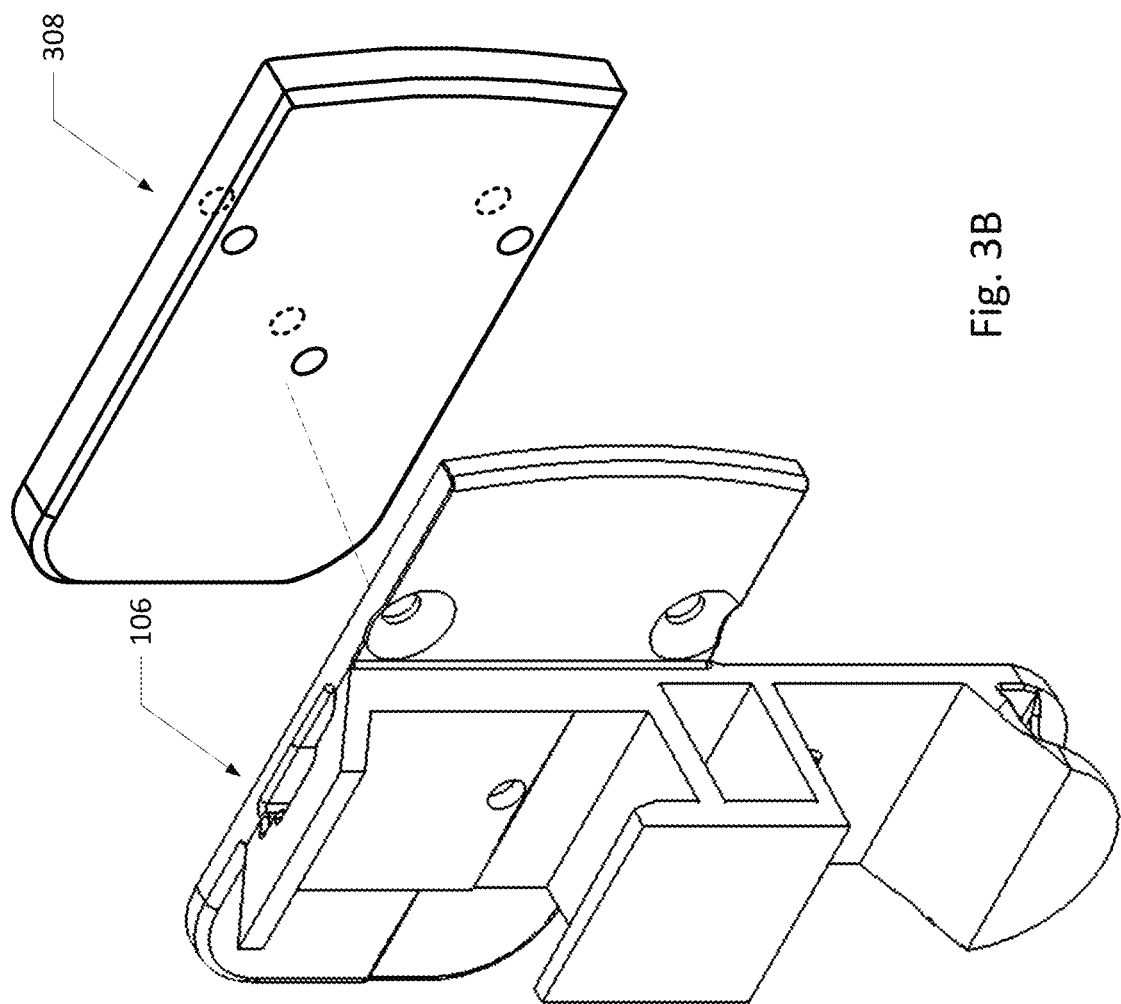

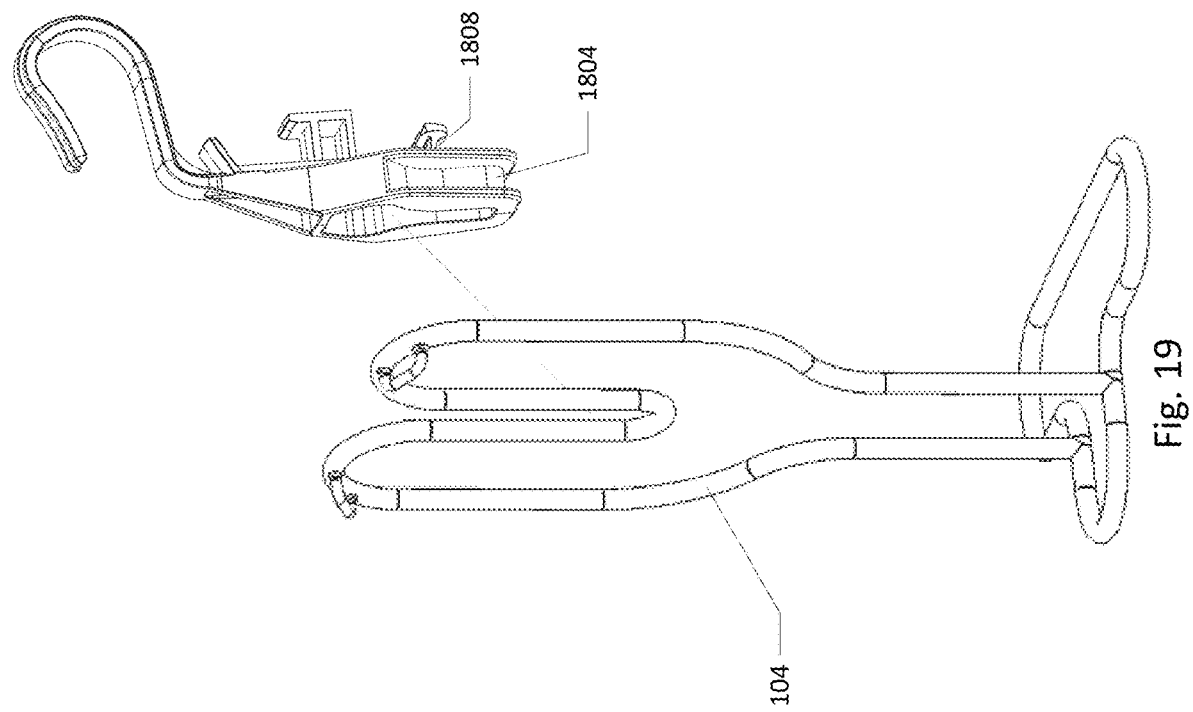
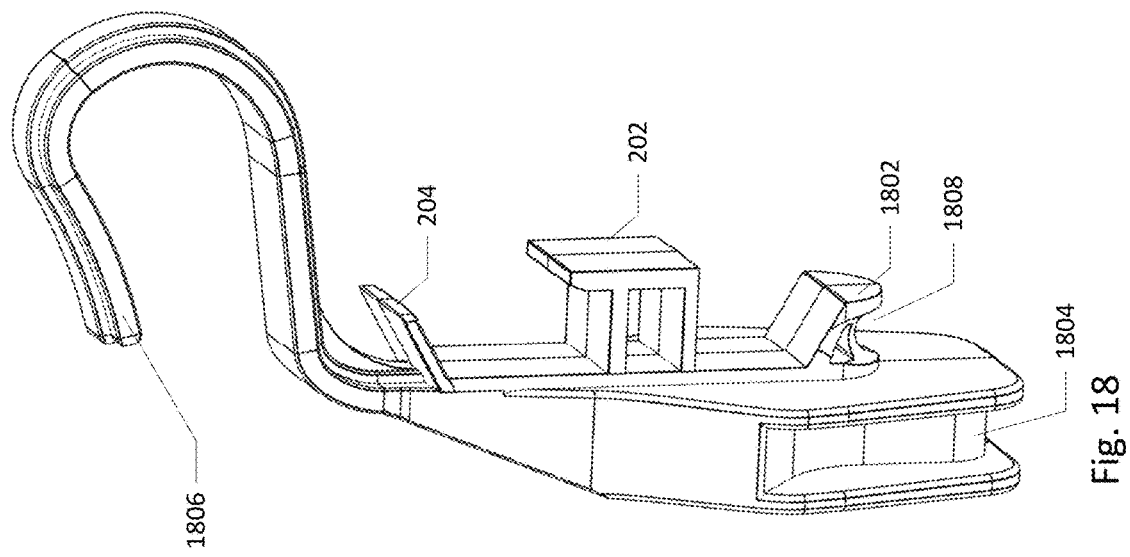

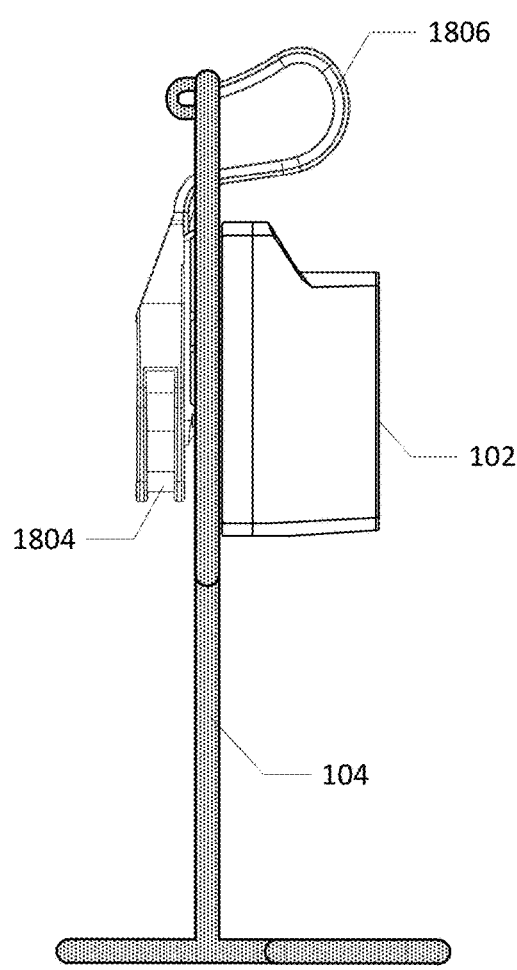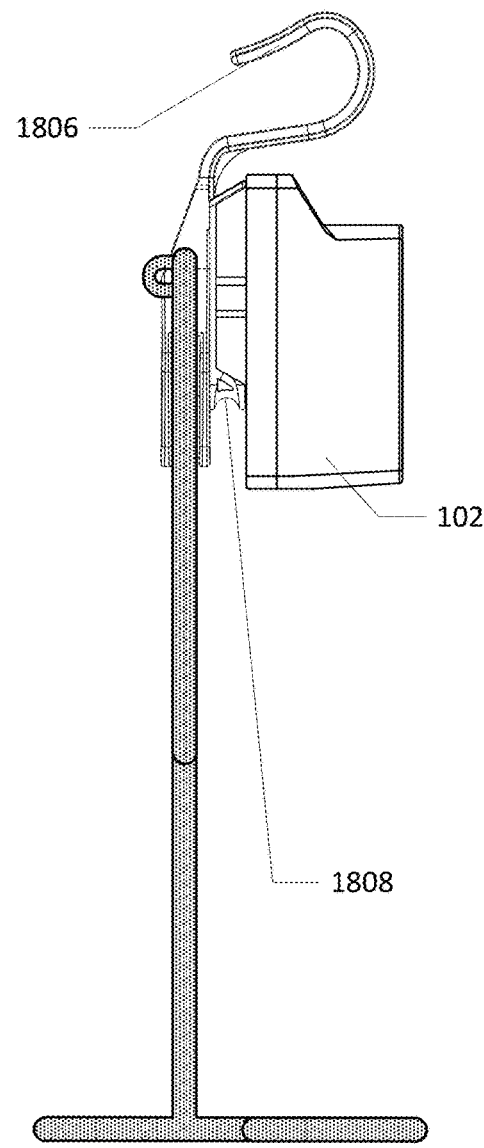
Fig. 20                    Fig. 21

EQUIPMENT ADAPTOR ASSEMBLY AND EQUIPMENT STAND

CROSS-REFERENCE TO RELATED APPLICATIONS

This application is a continuation of International Application No. PCT/US2022/013701 filed Jan. 25, 2022, which claims priority to U.S. Provisional Application No. 63/141,692 filed Jan. 26, 2021, each of which is herein incorporated by reference to the same extent as if such patent application were specifically and individually indicated to be so incorporated by reference.

FIELD

Embodiments disclosed herein relate to devices and methods for mounting equipment on different hardware and/or in different environments.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND

In a hospital or medical setting, different types of equipment are used to treat and/or monitor a patient. Often a patient is moved from room to room, for example from an intake room or hallway, to an operating room, to an intensive care unit, to a different type of hospital room, etc. In some cases, the medical equipment follows the patient from room to room. In some cases the medical equipment must accommodate different room configurations, different bed configurations, etc. For example, in some hospital rooms, IV poles may be available to hold equipment. In some rooms tables, or benches may be available to hold equipment. In some rooms, the equipment must follow the patient and be attached to the patient's bed. In some rooms, the equipment must be placed on the floor, or another surface.

Some medical equipment, for example, fluid drainage or collection equipment, needs to be maintained at a relatively level position to accurately determine the volume of liquid collected, or delivered. Maintaining equipment in a level position in these varied room/patient configurations is a challenge, especially in a highly charged and quickly changing environment, such as in a hospital.

SUMMARY

The adaptor assembly and floor stand disclosed herein address these mounting problems with medical equipment, or other types of equipment with similar challenges. The adaptor assembly attaches easily to a piece of medical equipment, allowing the equipment to be secured to a vertical pole, a horizontal pole or ledge, or, when used in conjunction with the floor stand, to be placed on the floor, or other surface.

One variation of the adaptor for supporting equipment from a support structure may generally comprise an adaptor body having a width and a depth, a connector extending from the adaptor body and configured for securement to the equipment, a first recess defined by a brace positioned at a first location along the adaptor body, and a second recess defined at a second location along the adaptor body at a distance from the first recess. The adaptor may be further configured to be interchangeably securable to a support structure via the first recess or the second recess while maintaining a level orientation of the equipment such that securement to the support structure via the first recess positions the equipment at a first height relative to horizontal and securement to the support structure via the second recess positions the equipment at a second height relative to horizontal where the first height and second height are different.

Another variation may include an apparatus for supporting equipment from a support structure generally comprising an adaptor body having a width and a depth, a connector extending from the adaptor body and configured for securement to the equipment, a first recess defined at a first location along the adaptor body, wherein securing the adaptor body to a support structure via the first recess maintains the adaptor body in a first level orientation at a first height, and a second recess defined at a second location along the adaptor body and separated from the first recess, wherein securing the adaptor body to the support structure via the second recess maintains the adaptor body in a second level orientation at a second height which is higher than the first height relative to the support structure.

BRIEF DESCRIPTION OF THE DRAWINGS

FIG. 3B shows an embodiment of a weighted plate for use with the adaptor assembly.

FIG. 18 shows another embodiment of the adaptor assembly.

FIG. 19 shows the adaptor assembly of FIG. 18, and how the adaptor engages a floor stand.

FIG. 20 shows a side view of the adaptor assembly of FIG. 18 engaged with a floor stand.

FIG. 21 shows a side view of the adaptor assembly of FIG. 18 engaged with a floor stand.

DETAILED DESCRIPTION

Figure 1:
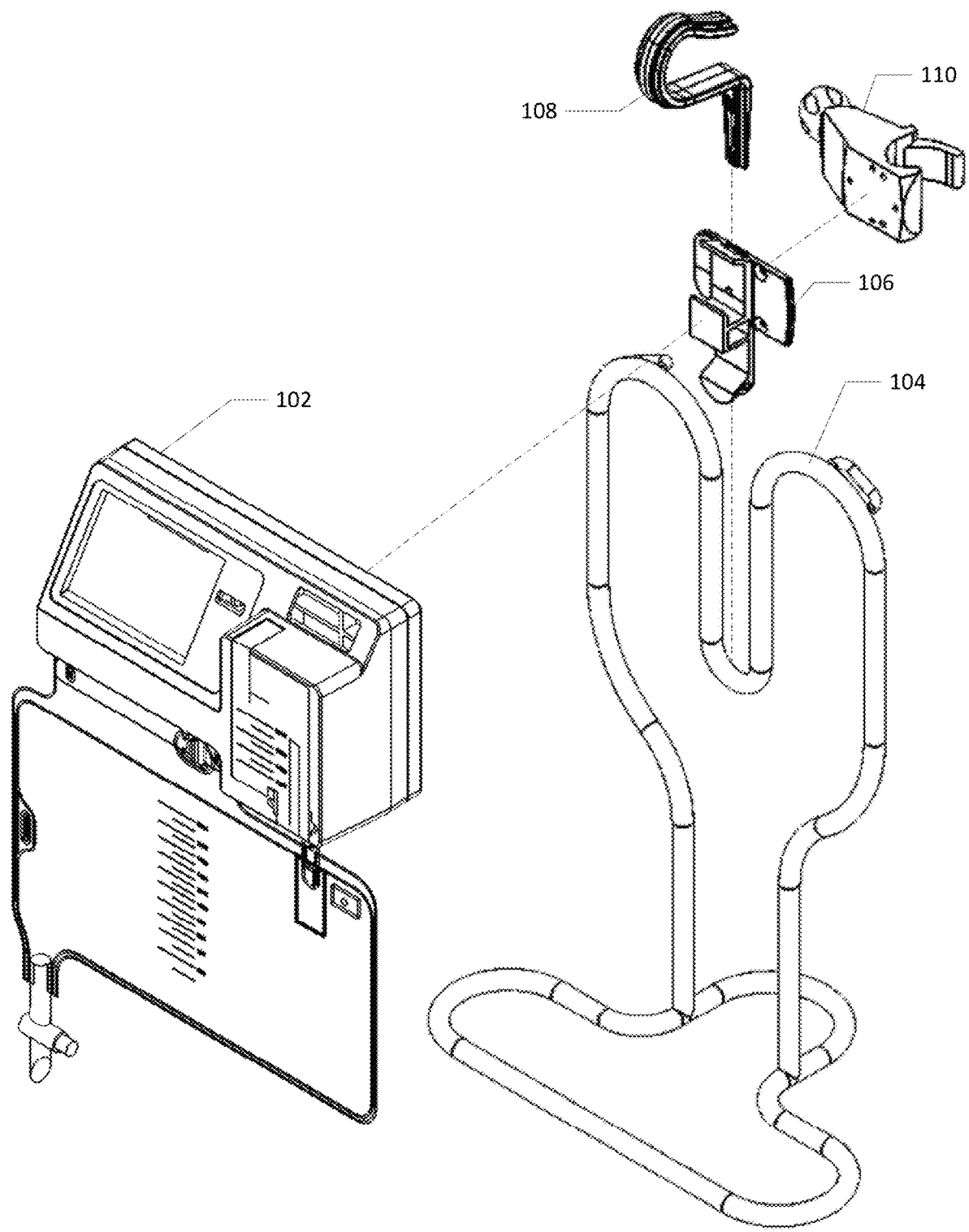
FIG. 1 shows an exploded view of an embodiment of the equipment adaptor assembly in use with the floor stand.

FIG. 1 shows an exploded view of an embodiment of the equipment adaptor assembly in use with a monitor and a stand. Shown here is monitor 102, which in this example, is a urine output and patient parameter monitor, for example as disclosed in U.S. patent application Ser. No. 13/414,011, filed on Mar. 7, 2012, U.S. patent application Ser. No. 13/809,043, filed on Apr. 1, 2013, PCT application WO/2014/043650, filed on Sep. 16, 2013, U.S. patent application Ser. No. 14/978,785, filed on Dec. 22, 2015, U.S. patent application Ser. No. 15/201,156, filed on Jul. 1, 2016, U.S. patent application Ser. No. 15/277,957, filed on Sep. 27, 2016, U.S. patent application Ser. No. 15/441,129, filed on Feb. 23, 2017, U.S. patent application Ser. No. 15/446,977, filed on Mar. 1, 2017, U.S. patent application Ser. No. 15/583,730, filed on May 1, 2017, each of which is herein incorporated by reference in its entirety. Although this monitor is shown here, any suitable equipment or monitor may be used. The equipment adaptor assembly includes adaptor 106, hook 108, and clamp 110. The equipment adaptor assembly is attached to the back of monitor 102 so that the monitor may be hung upright from a horizontal rail or pole or other horizontal support structure, a vertical rail or pole or other vertical support structure, or floor stand or support structure 104. Adaptor 106 may engage with floor stand 104. Hook 108 may engage with a horizontal rail or pole, such as a bed rail, or a horizontal surface, such as a table or bench. Clamp 110 may engage with a vertical pole, such as an IV pole. In this way, the adaptor assembly, when attached to monitor 102, allows the monitor to be hung upright, and off the floor, in any number of ways, allowing for flexibility in a hospital, or other medical, or other setting.

Figure 2:
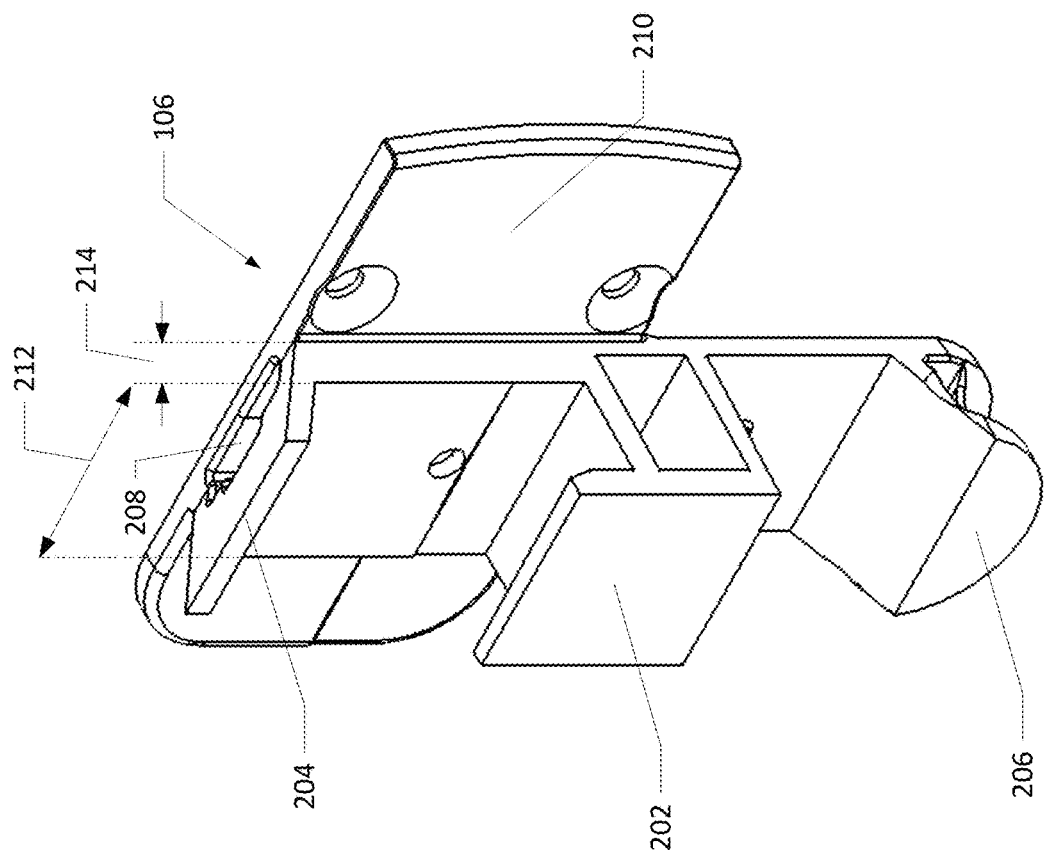
FIG. 2 shows a close-up view of an embodiment of the adaptor component of the adaptor assembly.

FIG. 2 shows a close-up view of an embodiment of adaptor 106. The adaptor includes connector 202, which is used to connect the adaptor to the equipment which is being mounted, such as monitor 102. Also included is top brace 204 and bottom brace 206, which contacts the surface of the equipment to stabilize the equipment relative to the adaptor, as well as secures the adaptor with respect to the floor stand. Hook stem opening 208 is configured to receive and secure the stem of hook 108. Adaptor plate 210 is configured to attach to clamp 110. The adaptor also has an adaptor width 212 and adaptor depth 214. The adaptor may be made out of polymer, metal, or any other suitable material. The adaptor portion of the adaptor assembly is configured to engage with a floor stand, as will be illustrated herein.

Figure 3A:
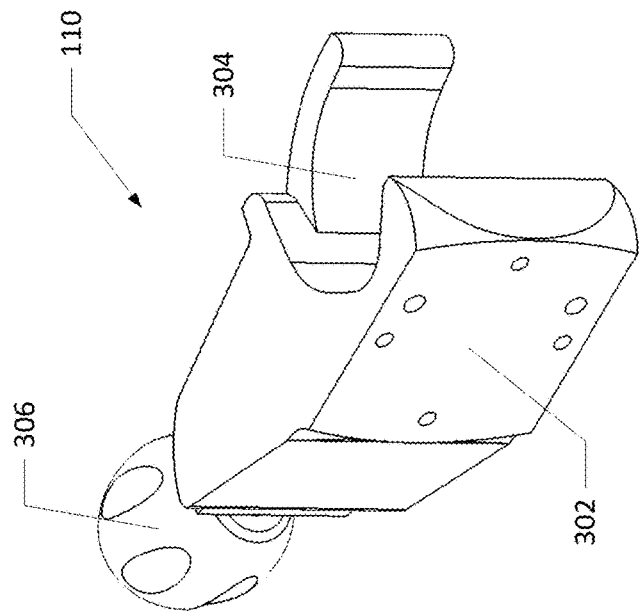
FIG. 3A shows an embodiment of the clamp component of the adaptor assembly.

FIG. 3A shows an embodiment of clamp 110. Shown are clamp plate 302, used to connect the clamp to adaptor 106 by connecting with adaptor plate 210, clamp grasper 304 and clamp tightening knob, 306, used to tighten and loosen the clamp grasper. The clamp portion of the adaptor assembly is configured to engage with a vertical rail or pole, as will be illustrated herein.

FIG. 3B shows an embodiment where clamp 110 is replaced by weighted plate 308. This embodiment is used in situations where a vertical pole mount is not required. Weighted plate 308 is weighted so that adaptor 106 is weight balanced in use and the monitor hanging on adaptor 106 is relatively level.

Figure 4:
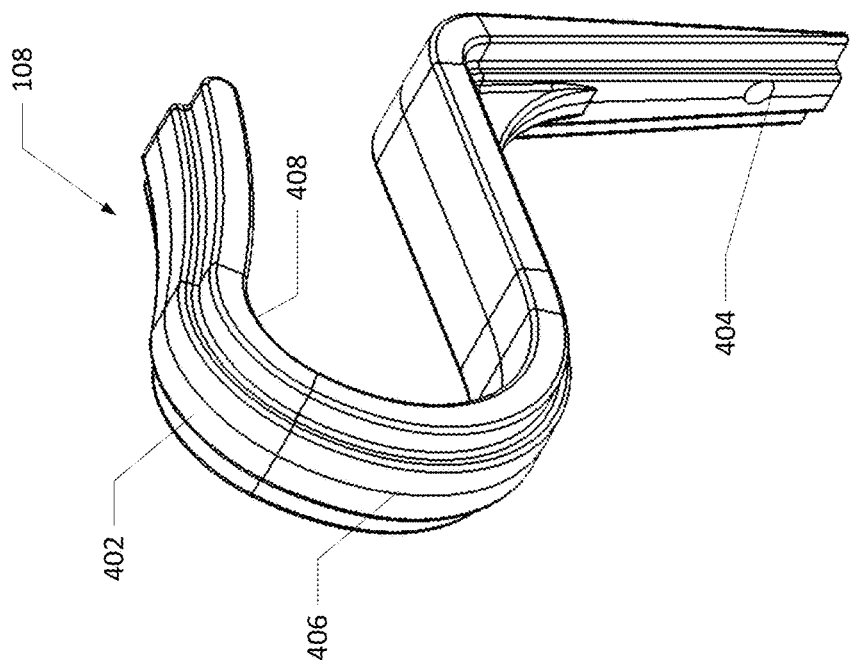
FIG. 4 shows an embodiment of the hook component of the adaptor assembly.

FIG. 4 shows an embodiment of hook 108. The hook includes hook head 402, hook stem 404, hook head curved portion 406 and hook head dip 408. The curve and the dip of the hook are designed so that the equipment held by the adaptor assembly is held upright, regardless of the angle of the rail/pole with which the hook is engaged. The hook design allows the equipment to self-level with the help of gravity. The hook design will "rock" on a horizontal pole so that that gravity pull the hanging equipment down so that it is level. This "rocking" may occur in either the front to back direction, or the side to side direction, or both, including any angles. The hook design may allow for up to 3 degrees of tilt of the monitor in any direction. Alternatively, the hook may allow for up to 5 degrees of tilt of the monitor in any direction. Alternatively, the hook may allow for up to 8 degrees of tilt of the monitor in any direction. Alternatively, the hook may allow for up to 10 degrees of tilt of the monitor in any direction.

Hook dip 408 also prevents the hook from accidentally falling off of a horizontal or essentially horizontal pole or rail. Hook stem 404 is inserted into hook stem opening 208 of the adaptor and secured, by screws or otherwise. The hook portion of the adaptor assembly is configured to engage with a substantially horizontal rail or pole or surface.

Figure 5:
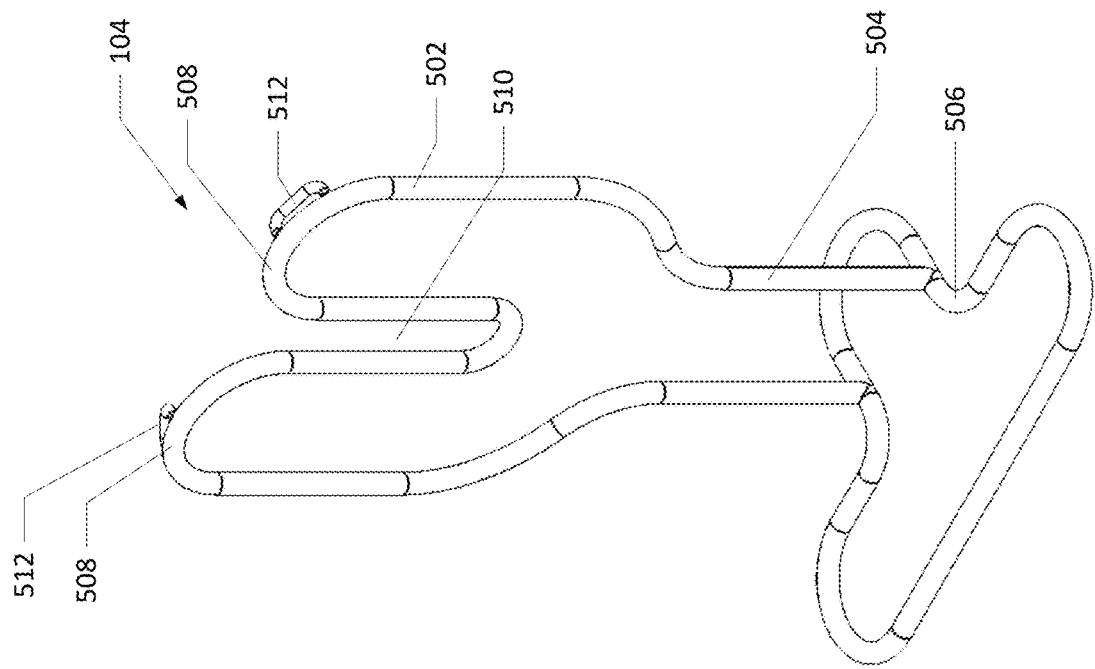
FIG. 5 shows an embodiment of the floor stand.

FIG. 5 shows an embodiment of floor stand 104. The floor stand includes stand stem 504, stand top area 502, which is an extension of stand stem 504, stand base 506, stand handles 508, stand top aperture 510 and stand extensions 512. Stand top aperture 510 is an aperture within stand top area 502, which is an extension of stand stem 504. Stand top area 502 is configured to stabilize and protect monitor 102. Aperture, or invagination, 510 is configured to receive and hold the adaptor assembly when the monitor is mounted on the floor stand. Stand stem is configured to hold the monitor up off of the floor, ideally so that no part of the monitor is touching the floor. Base 506 is configured to stabilize the stand and monitor so that tipping is minimal, while taking up minimal space on the floor. Handles 508 are configured to be used as handles, to lift the floor stand while the monitor is mounted on the floor stand. Handles 508 are also configured in some embodiments to protrude above the top of the monitor when the monitor is mounted on the stand so that a heavy force exerted on the top of the stand, such as a bed, or other heavy object coming down on the stand, will not damage the monitor. The stand may be made out of metal or other strong material so that it can withstand the force of a bed or other heavy object. Extensions 512 are configured to prevent mounting the monitor/adaptor assembly backwards, as it may be more susceptible to tipping. The extensions may also be used to mount the floor stand/monitor/adaptor assembly together onto a wall, pole, bed etc, via hooks or other suitable mounts.

Figure 6:
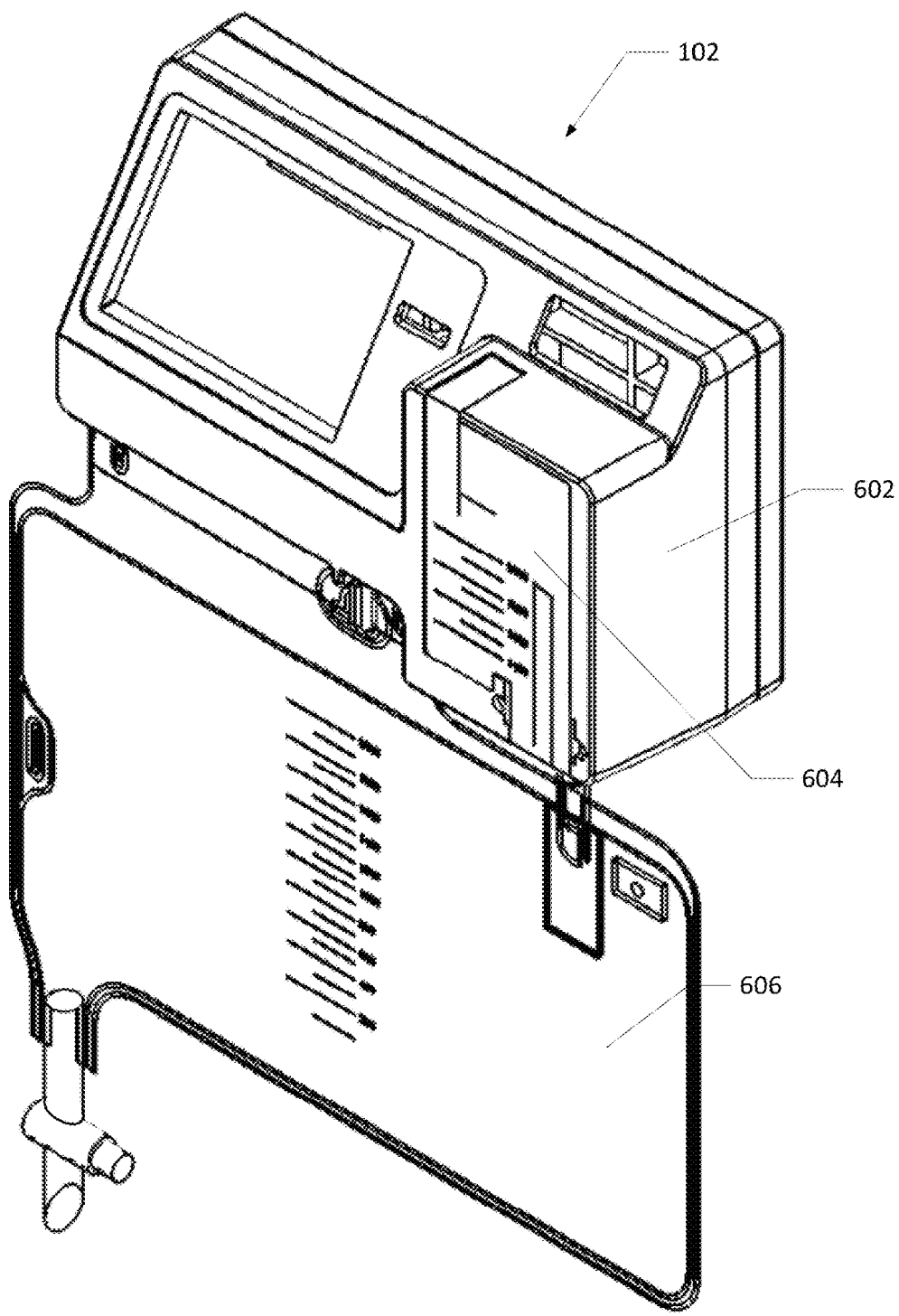
FIG. 6 shows an example of the type of equipment that may be mounted using the adaptor assembly.

FIG. 6 shows an example of the type of equipment that may be mounted using the adaptor assembly. The embodiments disclosed herein are particularly useful for medical equipment, but may be used with other types of equipment as well. For example, the adaptor assembly and/or stand may be used with urine drainage systems, chest drainage systems, wound drainage systems, any fluid drainage system, any monitor (for example, a monitor of vital signs, ECG, fluids, breathing etc.), ventilators, fluid infusion systems, dialysis systems, drug delivery systems, IV fluid systems, drug delivery systems, feeding pump systems, industrial monitors, industrial fluid management systems, etc.

The urine output management system shown in FIG. 6 includes controller component 602, fluid collection cassette 604 and fluid drainage bag 606. Similar systems are disclosed in U.S. patent application Ser. No. 13/414,011, filed on Mar. 7, 2012, U.S. patent application Ser. No. 13/809,043, filed on Apr. 1, 2013, PCT application WO/2014/043650, filed on Sep. 16, 2013, U.S. patent application Ser. No. 14/978,785, filed on Dec. 22, 2015, U.S. patent application Ser. No. 15/201,156, filed on Jul. 1, 2016, U.S. patent application Ser. No. 15/277,957, filed on Sep. 27, 2016, U.S. patent application Ser. No. 15/441,129, filed on Feb. 23, 2017, U.S. patent application Ser. No. 15/446,977, filed on Mar. 1, 2017, U.S. patent application Ser. No. 15/583,730, filed on May 1, 2017, each of which is incorporated herein by reference in its entirety.

The embodiments disclosed herein are particularly useful with devices/equipment which requires a certain amount of leveling, such as fluid management systems, fluid measurement systems, fluid drainage systems, etc.

Figure 7:
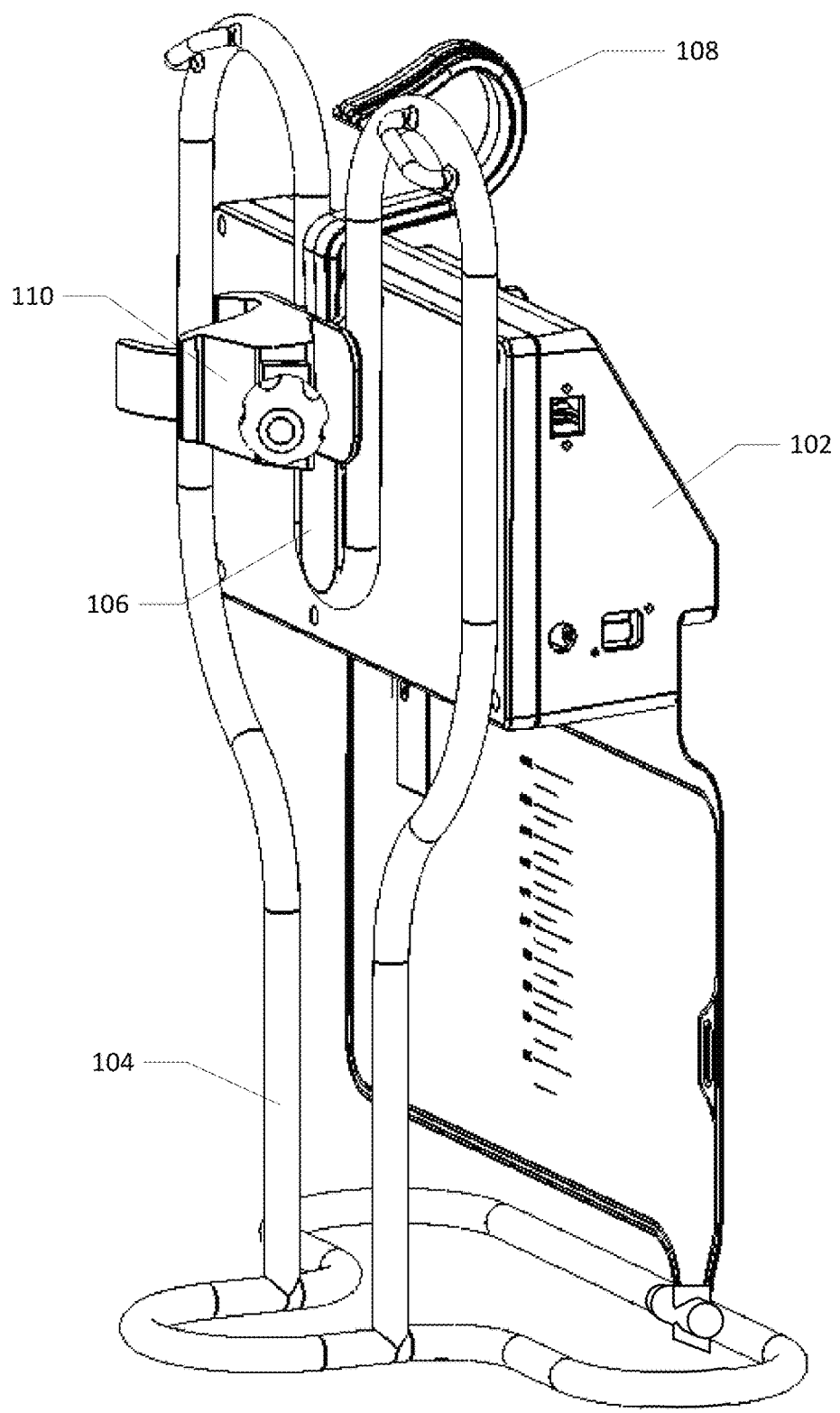
FIG. 7 shows the adaptor assembly and stand in use with the monitor.

FIG. 7 shows the adaptor assembly and stand in use with monitor 102. Adaptor assembly includes adaptor 106, hook 108, and clamp 110. Three components of the adaptor assembly are shown here, but in some embodiments, the assembly may include only 1 or 2 of these components, and/or other components may be included. The adaptor assembly slides into the top aperture of stand 104 from above until the bottom of adaptor 106 is engaged with the bottom of the stand aperture. The fit between adaptor 106 and stand 104 may be a snug or tight fit, or it may be a loose fit, allowing for some "play" between the adaptor assembly and the stand. This play allows for some leveling, or tilt reduction, of the monitor or equipment when it is positioned in the stand via the adaptor assembly. This will be illustrated further in the figures below.

FIG. 7 shows the adaptor of the adaptor assembly engaged with the stand. The clamp and hook components of the adaptor assembly are not engaged in this figure, but may be easily engaged onto a horizontal or vertical rail or pole or surface if the monitor use requires it. In other words, the monitor, while it is connected to the adaptor assembly, may be easily lifted up, by the hook, from the stand, allowing it to be separated from the stand, and hung or clamped in another position, using either the hook or the clamp. Alternatively, the entire stand, including the adaptor assembly and the monitor, may be lifted by using a stand handle(s).

The stand handles in FIG. 7 are shown to protrude above the monitor. Alternatively, the handles of the stand may be flush, or nearly flush with the top of the monitor, so that the monitor is protected from heavy forces from above (like a bed on top of the stand), but less handle area is available for lifting the stand/monitor combination. Stand handles 508 may also protrude above hook 108, to prevent damage to the hook.

Figure 8:
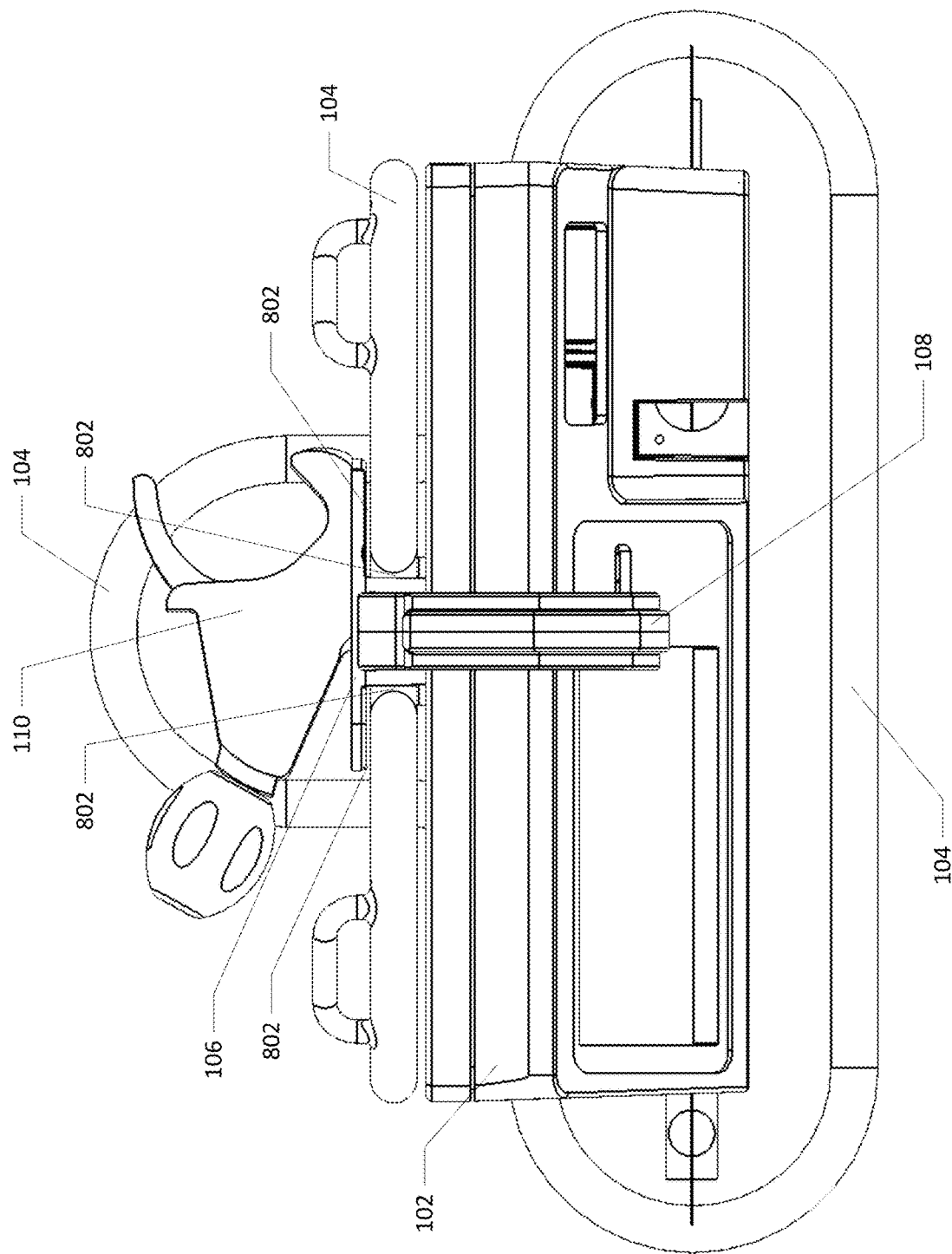
FIG. 8 shows a top view of the adaptor assembly engaged with the stand.

FIG. 8 shows a top view of the adaptor assembly engaged with the stand.

Adaptor assembly includes adaptor 106, hook 108, and clamp 110. The fit between adaptor 106 and stand 104 is shown here with a slightly loose fit, allowing for some "play" between the adaptor assembly and the stand. This play allows for some leveling, or tilt reduction, of the monitor or equipment when it is positioned in the stand via the adaptor assembly. These spaces, play, or tolerances between the stand and the adaptor are shown as spaces 802. This space may be around 0.10". Alternatively this space may be greater than around 0.05". Alternatively this space may be than around 0.05"-0.10". Alternatively this space may be than around 0.10"-0.20". Alternatively this space may be than around 0.20"-0.30". Alternatively this space may be than around 0.30"-0.40". Alternatively this space may be than around 0.40"-0.60". This space may allow for up to 3 degrees of tilt of the monitor in any direction. Alternatively, this space may allow for up to 5 degrees of tilt of the monitor in any direction. Alternatively, this space may allow for up to 8 degrees of tilt of the monitor in any direction. Alternatively, this space may allow for up to 10 degrees of tilt of the monitor in any direction, or both, or angles in between.

Figure 9:
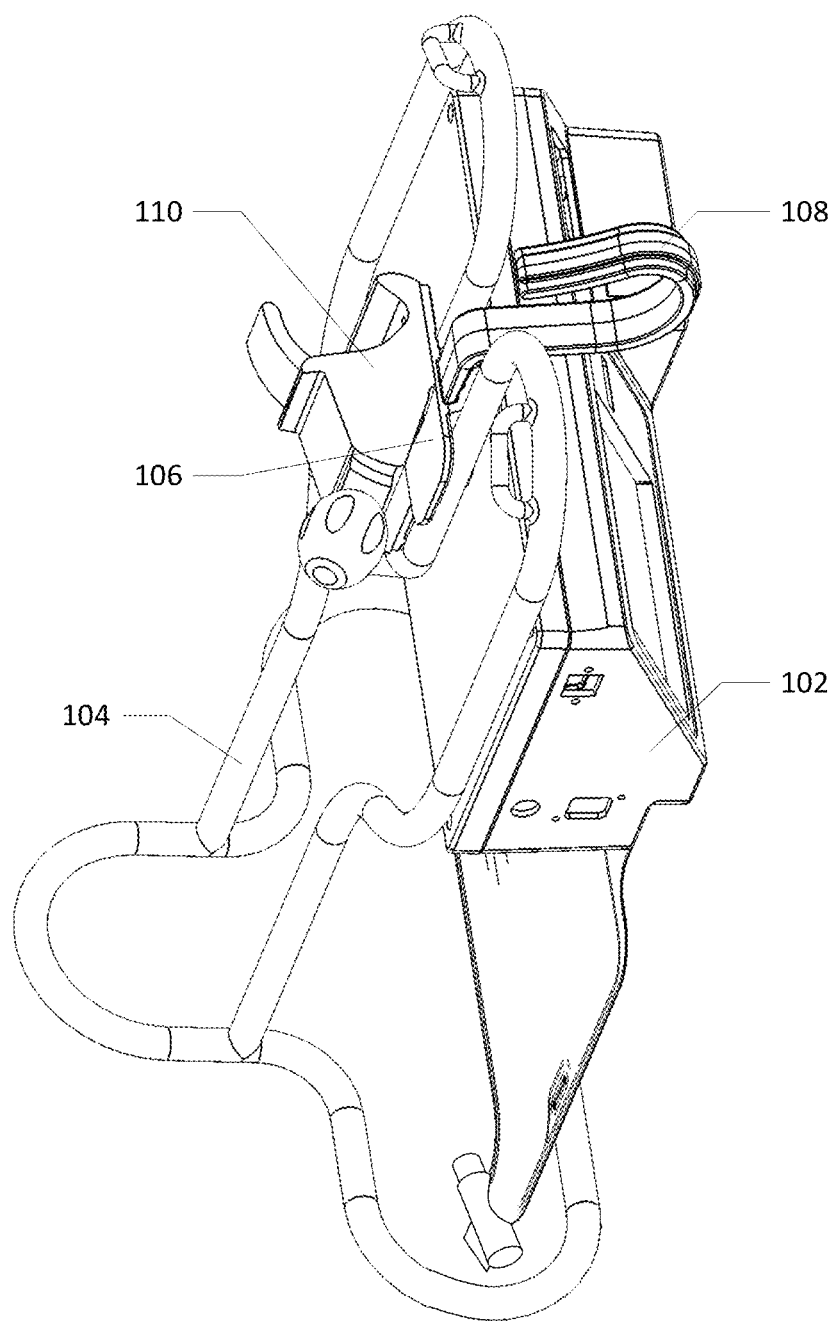
FIG. 9 shows an angled top view of the adaptor assembly engaged with the stand.

FIG. 9 shows an angled top view of the adaptor assembly engaged with the stand.

Figure 10:
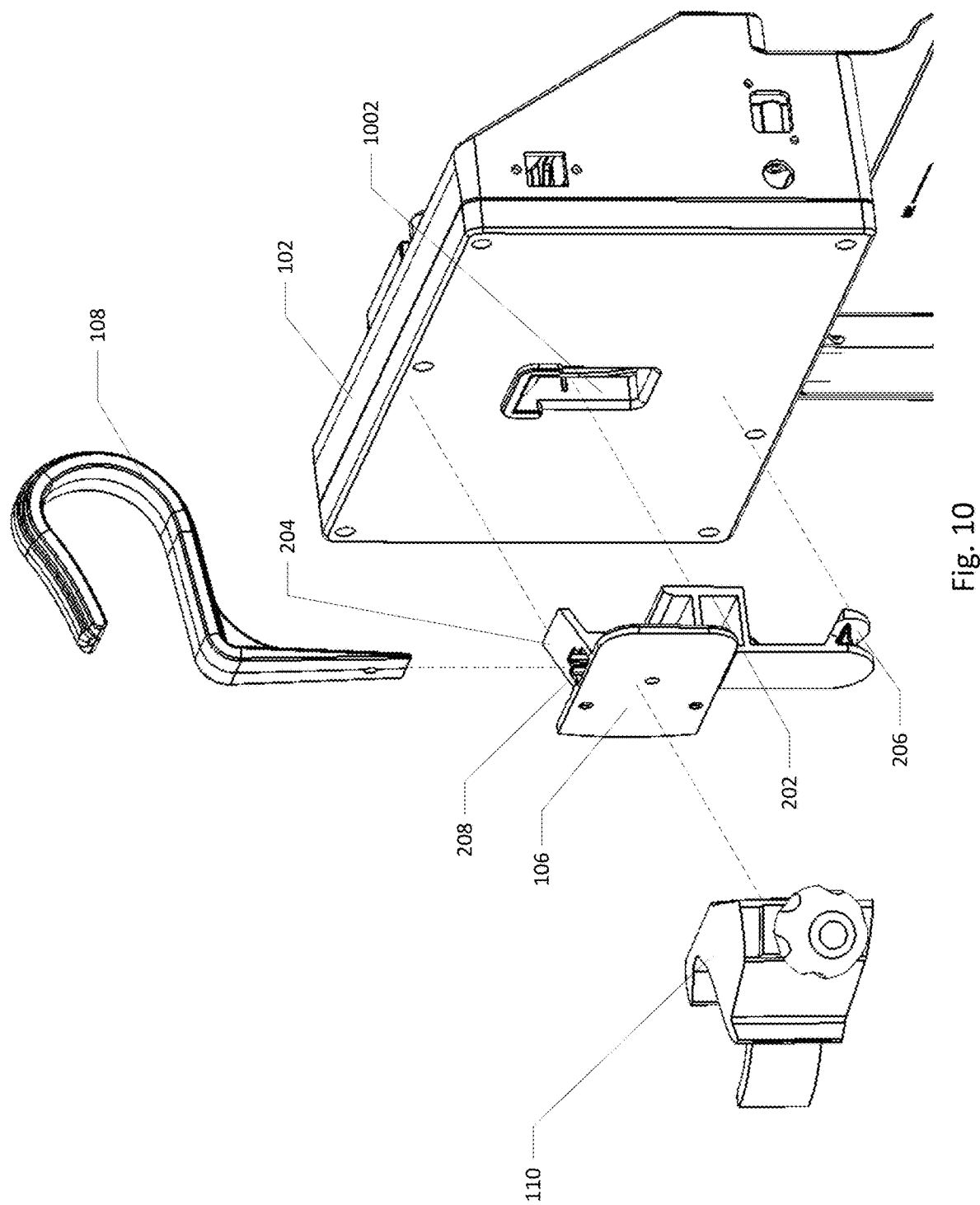
FIG. 10 shows an exploded view of the components of the adaptor assembly, as well as the back of the monitor.

FIG. 10 shows an exploded view of the components of the adaptor assembly, as well as the back of the monitor. Hook 108 is inserted into hook opening 208 of adaptor 106. The hook may be secured with screws, adhesive, friction etc. Clamp 110 is attached to adaptor 106 similarly. Connector 202 of adaptor 106 is inserted into monitor opening 1002 of monitor 102 so that the top and bottom braces (204 and 206) of the adaptor are flush against the back of the monitor, stabilizing the adaptor assembly with respect to the monitor. The connection between the adaptor and the monitor may be a reversible connection, so that the user can easily remove the adaptor assembly for storage, or for other reasons.

Figure 11:
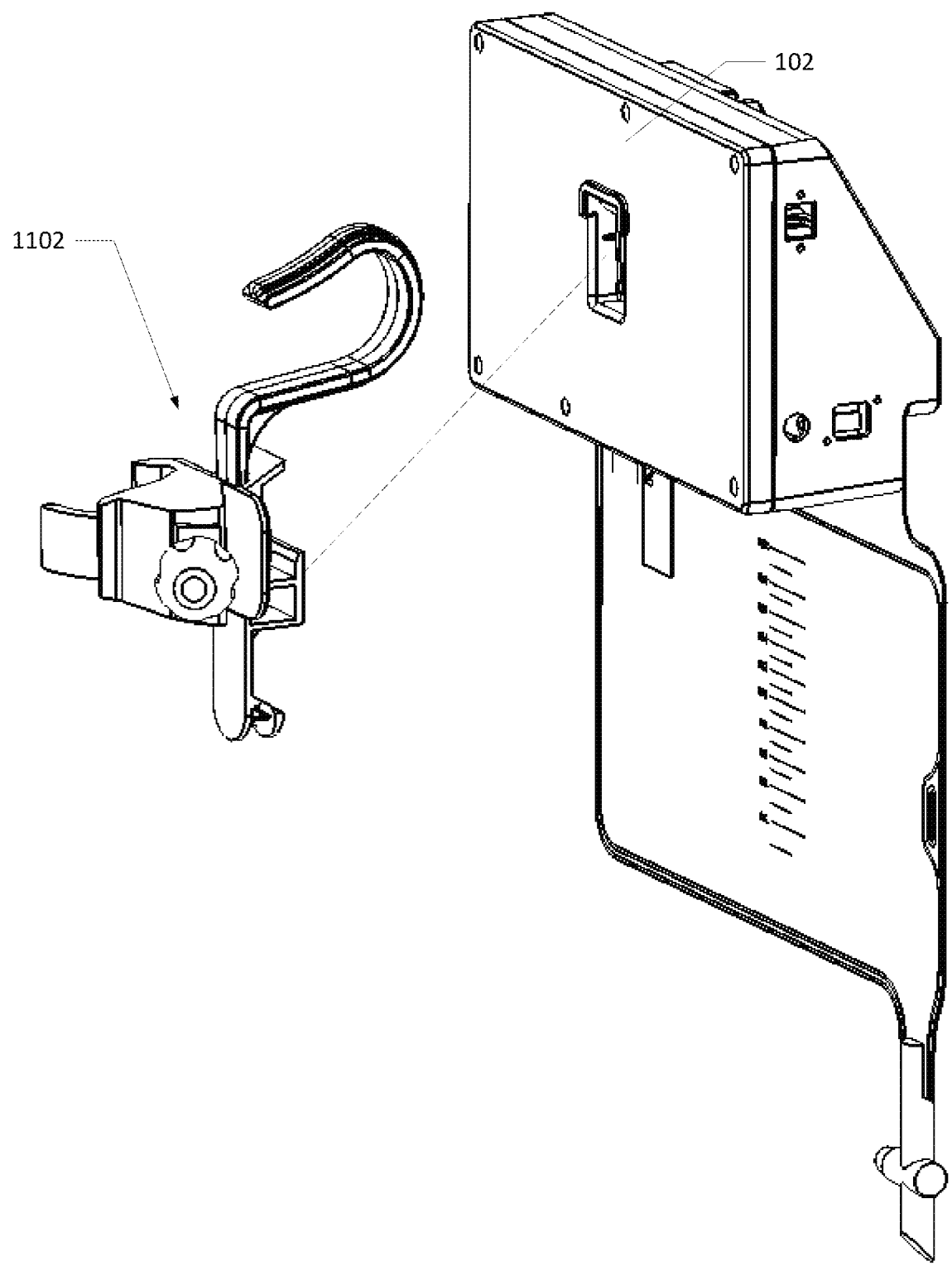
FIG. 11 shows the adaptor assembly in its assembled form, and how it connects with the monitor.

FIG. 11 shows adaptor assembly 1102 in its assembled form, and how it connects with monitor 102.

Figure 12:
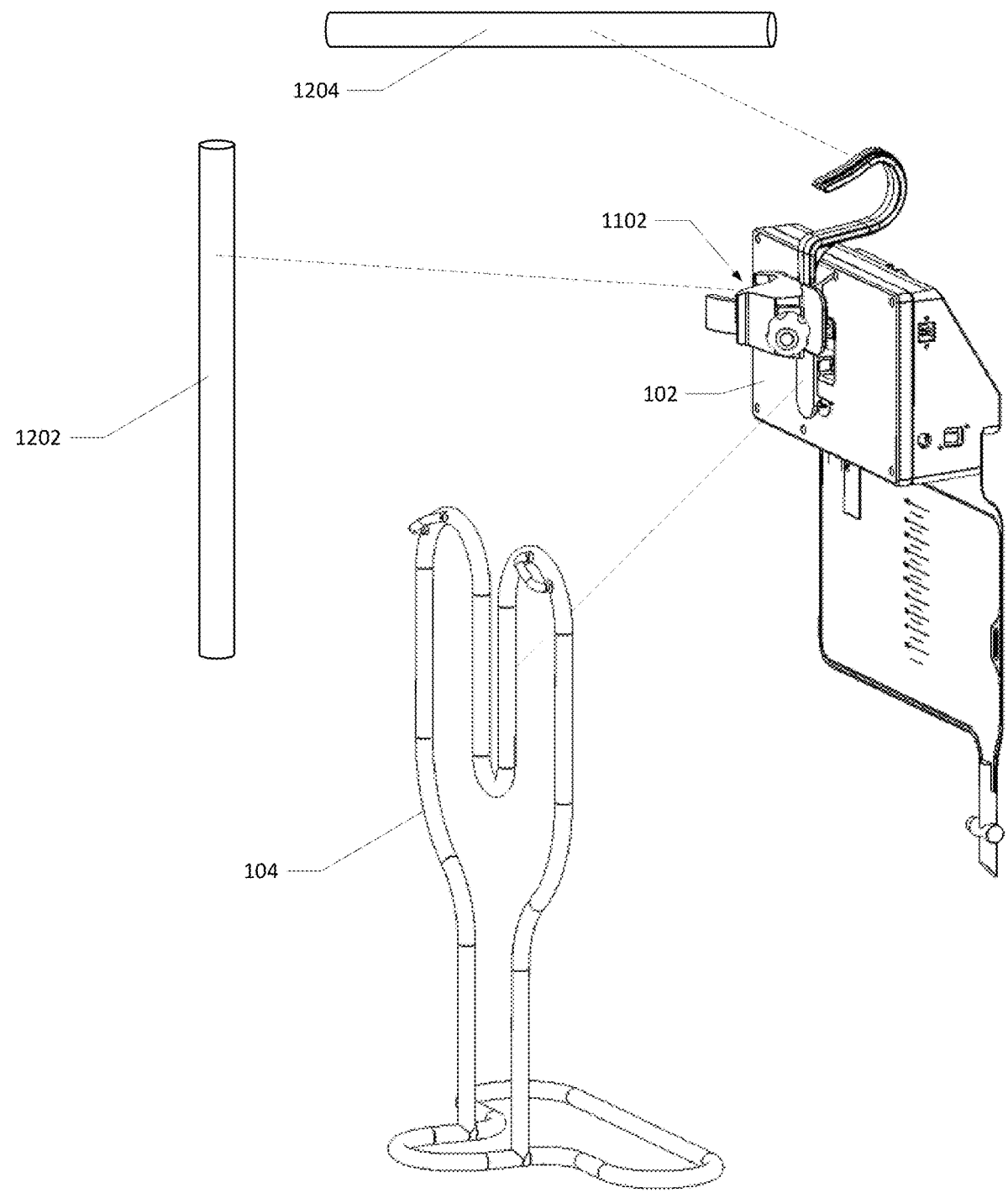
FIG. 12 shows the adaptor assembly's ability to mount, and in some circumstances, level, the monitor in virtually any environment.

FIG. 12 shows the adaptor assembly's ability to mount, and in some circumstances, level, the monitor in virtually any environment. The clamp component of the adaptor assembly may engage with vertical pole 1202, such as an IV pole. Alternatively, the hook component of the adaptor assembly may engage with horizontal pole, or rail, or surface 1204, such as a bed rail or table. The adaptor component of the adaptor assembly may engage with floor stand 104, for placement on the floor, or table or other flat surface. Any of these configuration can be achieved, or changed, with minimal disturbance to monitor 102. In some embodiments, the adaptor assembly can be used to mount the monitor on a different type of structure (horizontal, vertical or floor) without rearranging the adapter assembly. In other words, the only necessary action to move the adaptor assembly from one type of structure to another, may be the opening and closing of clamp 110 (which herein will not be considered "rearranging"). In some scenarios, for example, moving the adaptor assembly from the floor stand to a bed frame or horizontal pole/surface or vice versa, no rearrangement of the adaptor assembly needs to be done, and in addition, clamp 110 need not be opened or closed. This is important because at times these types of switches (from the floor to a bed for example) may need to be performed in a hurry. There is not often time to rearrange the adaptor so that it can connect to a different type of structure.

In some embodiments, the adaptor can mount to a horizontal surface (including a pole), vertical surface (including a pole) and a floor stand. In some embodiments, the adaptor can mount to a vertical surface and a floor stand. In some embodiments, the adaptor can mount to a horizontal surface and a floor stand. In some embodiments, the adaptor can mount to a horizontal surface and a vertical surface. In some embodiments, the adaptor can mount to any one of a horizontal surface, a vertical surface or a floor stand.

Figure 13:
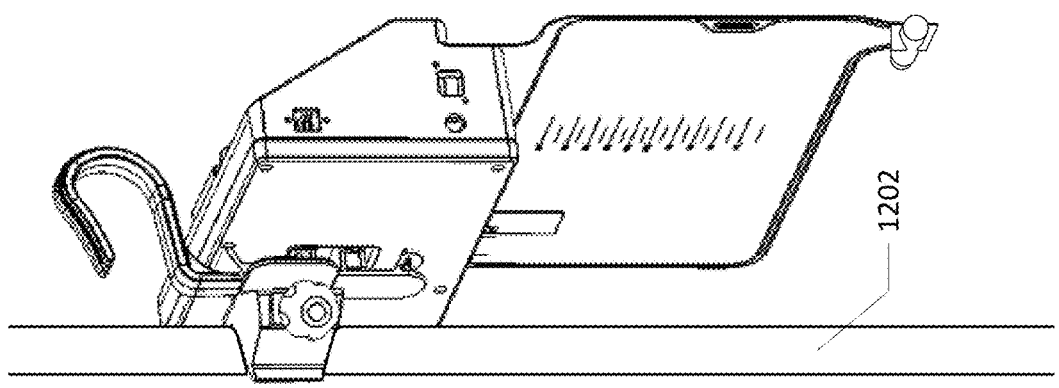
FIG. 13 shows the adaptor assembly/monitor engaged with a vertical pole.

FIG. 13 shows the adaptor assembly/monitor engaged with vertical pole 1202.

Figure 14:
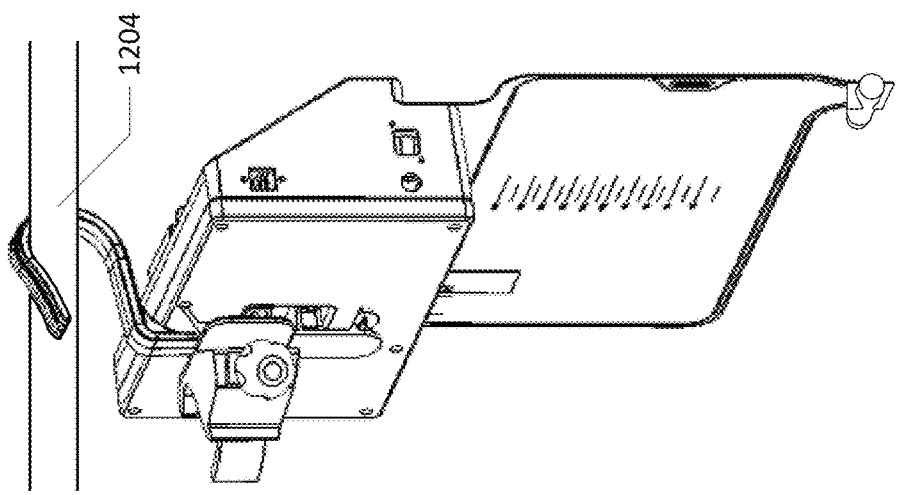
FIG. 14 shows the adaptor assembly/monitor engaged with a horizontal pole.

FIG. 14 shows the adaptor assembly/monitor engaged with horizontal pole 1204.

Figure 15:
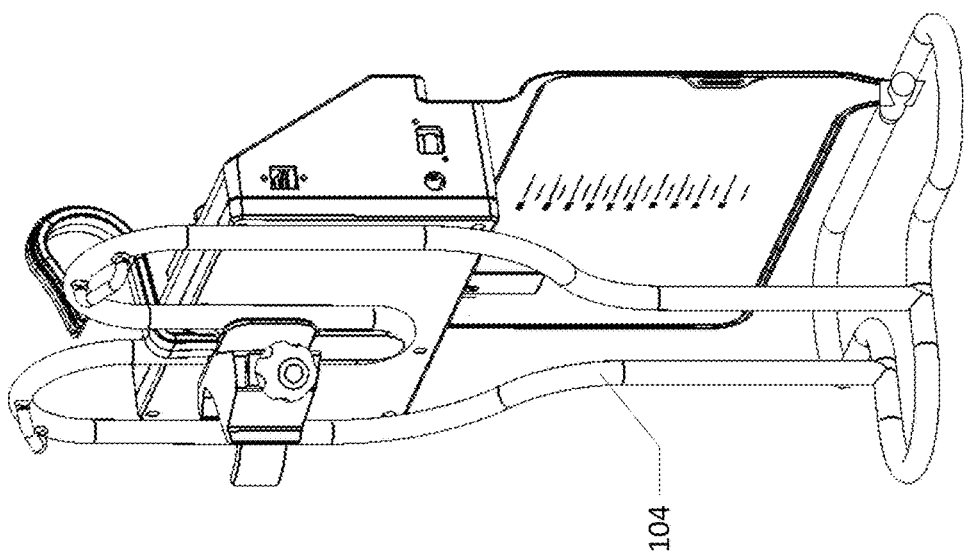
FIG. 15 shows the adaptor assembly/monitor engaged with the floor stand.

FIG. 15 shows the adaptor assembly/monitor engaged with floor stand 104.

Figure 17:
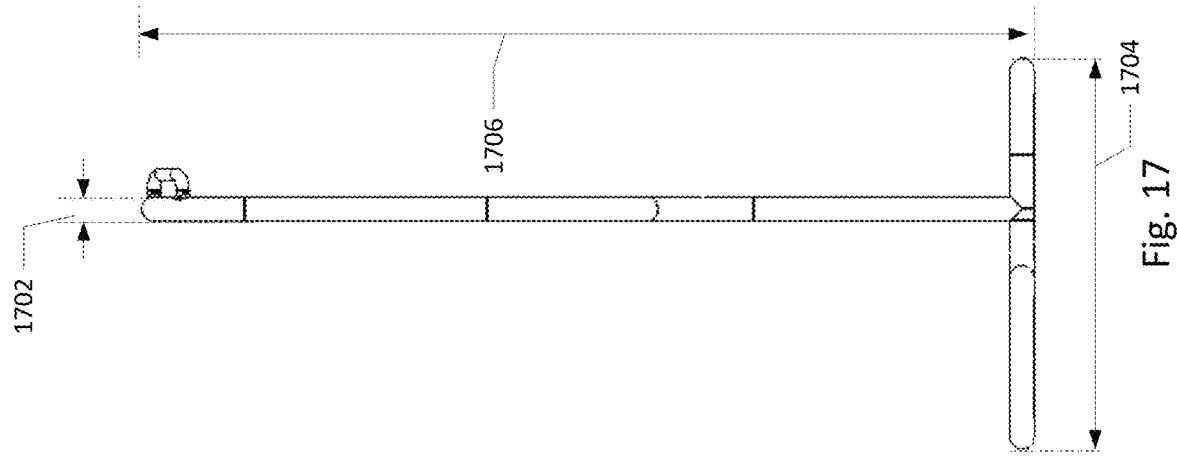
FIGS. 16 and 17 show dimensional detail of the floor stand.
Figure 16:
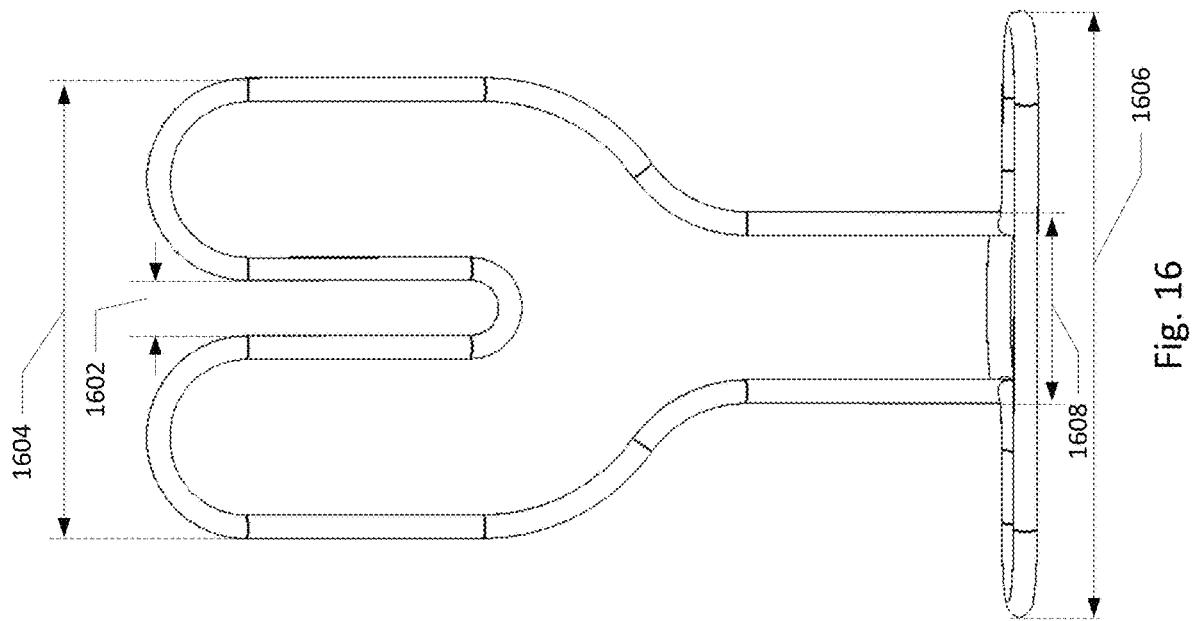

FIGS. 16 and 17 show dimensional detail of the floor stand. Stand aperture width 1602 is sized to accept the adaptor portion of the adaptor assembly, such that stand aperture width 1602 is larger than adaptor width 212, shown in FIG. 2. The larger the difference in width between the stand aperture and the adaptor width, the more side to side "play" results. Stand top aperture depth 1702 is sized to accept the adaptor portion of the adaptor assembly, such that stand aperture depth 1702 is larger than adaptor depth 214, shown in FIG. 2. The larger the difference in depth between the stand aperture and the adaptor depth, the more front to back "play" results. The more "play" between the stand and the adaptor, the more the floor (or surface on which the stand is placed) may be tilted, while allowing the monitor remain level, when engaged in the stand. In other words, the "play" between the stand and the adaptor allows the monitor to hang level (by force of gravity) even if the stand is placed on a non-level surface.

Stand top width 1604 is configured to protect the monitor. The stand top width may be at least as wide as the width of the monitor, so that the monitor sides do not extend beyond the sides of the stand. This embodiment shows a stand with a fixed top width, however the width may be adjustable, to accommodate equipment of different sizes.

Stand base width 1606 is configured to maximize stability of the stand, while minimizing the footprint of the stand. In some embodiments shown herein, a fluid drainage bag hangs below the monitor. The stand base width may be at least as wide as the width of the fluid drainage bag to help prevent damage to the fluid drainage bag. This embodiment shows a stand with a fixed base width, however the width may be adjustable, to accommodate equipment of different sizes.

Stand stem width 1608 is shown in this embodiment to be smaller than stand top width 1604 and stand base width 1606. This is to reduce the chances of users kicking or knocking the stand when it is in use. This embodiment shows a stand with a fixed width stem, however the width may be adjustable, to accommodate equipment of different sizes.

Stand base depth 1704 is configures to maximize stability of the stand, while minimizing the footprint of the stand. It is also designed to support the weight of the monitor which sits forward on the stand. In this embodiment, the front of the stand base is deeper than the back of the stand base for this reason. This embodiment shows a stand with a fixed depth, however the depth may be adjustable, to accommodate equipment of different sizes.

Stand height 1706 is configured to hold the monitor and any fluid drainage bag off of the floor. This embodiment shows a stand with a fixed height, however the height may be adjustable, to accommodate equipment of different sizes.

For example, stand height 1706 may be around 15-25 inches. Stand height 1706 may be around 19-21 inches.

Base depth 1704 may be around 8-11 inches. Base depth 1704 may be around 9-11 inches.

Stem width 1608 may be around 3-6 inches. Stem width 1608 may be around 4-5 inches.

Base width 1606 may be around 10-15 inches. Base width 1606 may be around 13-14 inches.

Stand aperture width 1602 may be around 1-4 inches. Stand aperture width 1602 may be around 1-2 inches.

Stand width 1604 may be around 10-15 inches. Stand width 1604 may be around 13-14 inches.

FIG. 18 shows another embodiment of the adaptor assembly. The adaptor includes connector 202, which is used to connect the adaptor to the equipment which is being mounted, such as monitor 102. Also included is top brace 204 and bottom brace 1802, which includes first recess 1808. Bottom brace 1802 contacts the surface of the equipment to stabilize the equipment relative to the adaptor, as well as secures the adaptor with respect to the floor stand. Hook 1806 is shown and may be incorporated into the adapter assembly. This embodiment also includes secondary recess 1804, which may be used to secure the adaptor to the floor stand so that the equipment rests further from the floor. In this way, this adapter may be used to stabilize the equipment within the stand at two or more levels, or positions. The lower level may be used during fluid drainage, and the higher level may be used to empty the fluid drainage bag. This embodiment may or may not include a clamp, such as clamp 110 shown in FIG. 1. This embodiment may or may not include a weighted plate, such as plate 308, or an adaptor plate, as shown in FIG. 3B.

FIG. 19 shows the adaptor assembly of FIG. 18, and how the adaptor engages floor stand 104.

FIG. 20 shows a side view of the adaptor assembly of FIG. 18 engaged with floor stand 104 so that first recess 1808 is engaged in the floor stand aperture. This mode allows the equipment, such as monitor 102, to sit lower on the floor stand, i.e. closer to the floor.

FIG. 21 shows a side view of the adaptor assembly of FIG. 18 engaged with floor stand 104 so that secondary recess 1804 is engaged in the floor stand aperture. This mode allows the equipment, such as monitor 102, to sit higher on the floor stand, i.e. further to the floor. This mode may be useful when emptying the fluid drainage bag (not shown here).

Figure 22:
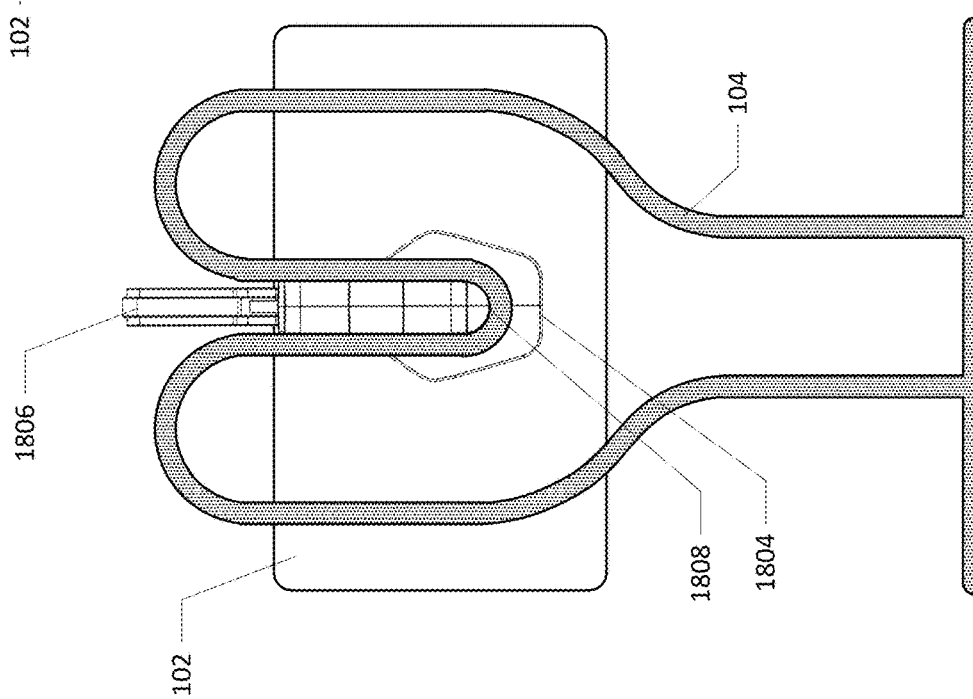
FIG. 22 shows a back view of the adaptor assembly of FIG. 18 engaged with a floor stand.

FIG. 22 shows a back view of the adaptor assembly of FIG. 18 engaged with floor stand 104 so that first recess 1808 is engaged in the floor stand aperture. This mode allows the equipment, such as monitor 102, to sit lower on the floor stand, i.e. closer to the floor.

Figure 23:
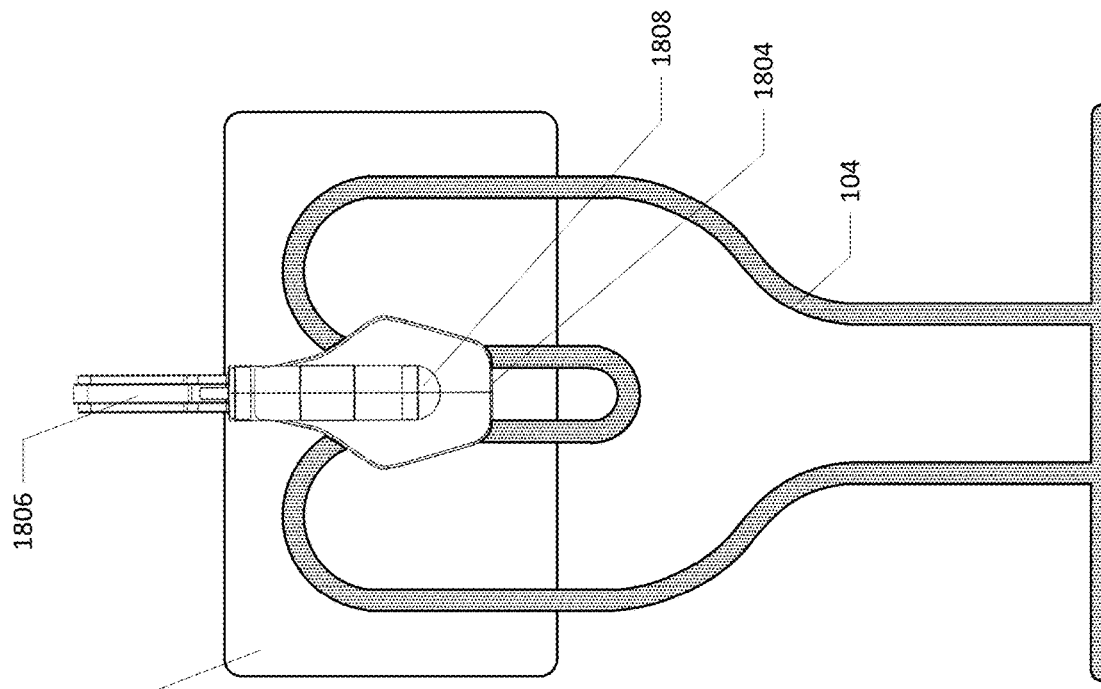
FIG. 23 shows a back view of the adaptor assembly of FIG. 18 engaged with a floor stand.

FIG. 23 shows a back view of the adaptor assembly of FIG. 18 engaged with floor stand 104 so that secondary recess 1804 is engaged in the floor stand aperture. This mode allows the equipment, such as monitor 102, to sit higher on the floor stand, i.e. further to the floor. This mode may be useful when emptying the fluid drainage bag (not shown here).

From the foregoing, it will be appreciated that specific embodiments of the invention have been described herein for purposes of illustration, but that various modifications may be made without deviating from the spirit and scope of the various embodiments of the invention. For example, several embodiments may include various suitable combinations of components, devices and/or systems from any of the embodiments described herein. Further, while various advantages associated with certain embodiments of the invention have been described above in the context of those embodiments, other embodiments may also exhibit such advantages, and not all embodiments need necessarily exhibit such advantages to fall within the scope of the invention.

What is claimed is:
1. An adaptor for supporting equipment, comprising:
an adaptor body having a width and a depth;
a connector extending from the adaptor body and configured for securement to the equipment;
a first recess defined by a brace positioned at a first location along the adaptor body; and
a second recess which is defined at a second location along the adaptor body at a distance distal to the first recess, wherein the adaptor is configured to be interchangeably securable to a support structure via the first recess or the second recess while maintaining a level orientation of the equipment such that securement to the support structure via the first recess engages the first recess to a first location along the support structure and positions the equipment at a first height relative to horizontal and securement to the support structure via the second recess engages the second recess to a second location along the support structure and positions the equipment at a second height relative to horizontal where the first height and second height are different.

2. The adaptor of claim 1 further comprising the equipment.

3. The adaptor of claim 2 wherein the equipment comprises a fluid drainage system.

4. The adaptor of claim 3 wherein the fluid drainage system is configured to monitor a volume of fluid drained from a patient body.

5. The adaptor of claim 4 wherein the fluid comprises urine.

6. The adaptor of claim 1 wherein the support structure comprises a floor stand.

7. The adaptor of claim 6 wherein the floor stand comprises:
a stand base;
one or more stand stem members extending from the stand base; and
a stand top area configured to form a stand aperture which is defined between two apposed portions of the stand stem members,
wherein the stand aperture is sized to slidingly receive the width of the adaptor body between the two apposed portions of the stand stem members.

8. The adaptor of claim 1 wherein the connector is configured to be releasably secured to the equipment.

9. The adaptor of claim 1 further comprising a hook defined along the adaptor body such that the hook projects away from the adaptor body when secured to the adaptor body.

10. The adaptor of claim 1 wherein the adaptor is interchangeably securable to the support structure via the first recess or the second recess while maintaining the level orientation of up to 10 degrees relative to horizontal.

11. An apparatus for supporting equipment, comprising:
an adaptor body having a width and a depth;
a connector extending from the adaptor body and configured for securement to the equipment;
a first recess defined at a first location along the adaptor body, wherein securing the adaptor body to a support structure via the first recess engages the first recess to a first location along the support structure and maintains the adaptor body in a first level orientation at a first height; and
a second recess which is defined at a second location along the adaptor body and separated distal to the first recess, wherein securing the adaptor body to the support structure via the second recess engages the second recess to a second location along the support structure and maintains the adaptor body in a second level orientation at a second height which is higher than the first height relative to the support structure.

12. The apparatus of claim 11 further comprising the equipment.

13. The apparatus of claim 12 wherein the equipment comprises a fluid drainage system.

14. The apparatus of claim 13 wherein the fluid drainage system is configured to monitor a volume of fluid drained from a patient body.

15. The apparatus of claim 14 wherein the fluid comprises urine.

16. The apparatus of claim 11 wherein the support structure comprises a floor stand.

17. The apparatus of claim 16 wherein the floor stand comprises:
a stand base;
one or more stand stem members extending from the stand base; and
a stand top area configured to form a stand aperture which is defined between two apposed portions of the stand stem members,
wherein the stand aperture is sized to slidingly receive the width of the adaptor body between the two apposed portions of the stand stem members.

18. The apparatus of claim 11 wherein the connector is configured to be releasably secured to the equipment.

19. The apparatus of claim 11 further comprising a hook defined along the adaptor body such that the hook projects away from the adaptor body when secured to the adaptor body.

20. The apparatus of claim 11 wherein the adaptor is interchangeably securable to the support structure via the first recess or the second recess while maintaining the level orientation of up to 10 degrees relative to horizontal.

21. The adaptor of claim 1 wherein the first recess has a first width and the second recess has a second width which is greater than the first width.

22. The apparatus of claim 11 wherein the first recess has a first width and the second recess has a second width which is greater than the first width.

* * * * *